US010966757B2

(12) United States Patent
Drozd et al.

(10) Patent No.: US 10,966,757 B2
(45) Date of Patent: Apr. 6, 2021

(54) VERTEBRAL ASSIST SPINAL MEDICAL DEVICE

(71) Applicant: ANDRO Computational Solutions LLC

(72) Inventors: Evan M. Drozd, Rome, NY (US); Jithin Jagannath, Rome, NY (US); Nicholas Joseph Polosky, Rome, NY (US); Andrew Louis Drozd, Rome, NY (US); Michael E. Garlington, Rome, NY (US)

(73) Assignee: ANDRO COMPUTATIONAL SOLUTIONS LLC, Rome, NY (US)

( * ) Notice: Subject to any disclaimer, the term of this patent is extended or adjusted under 35 U.S.C. 154(b) by 53 days.

(21) Appl. No.: 16/296,729

(22) Filed: Mar. 8, 2019

(65) Prior Publication Data

US 2019/0274735 A1  Sep. 12, 2019

Related U.S. Application Data

(60) Provisional application No. 62/640,904, filed on Mar. 9, 2018.

(51) Int. Cl.
  *A61B 17/70* (2006.01)
  *A61F 2/48* (2006.01)
  *A61B 17/00* (2006.01)

(52) U.S. Cl.
  CPC ...... *A61B 17/7017* (2013.01); *A61B 17/7016* (2013.01); *A61B 17/7074* (2013.01); *A61B 2017/0011* (2013.01); *A61B 2017/00022* (2013.01); *A61B 2017/00106* (2013.01); *A61B 2017/00212* (2013.01);
  (Continued)

(58) Field of Classification Search
  CPC ............ A61B 17/7016; A61B 17/7017; A61B 17/7074; A61B 17/7002; A61B 17/7019; A61B 17/7023; A61B 17/7025; A61B 2017/00022
  See application file for complete search history.

(56) References Cited

U.S. PATENT DOCUMENTS

| 8,282,671 B2 | 10/2012 | Connor |
| 8,641,723 B2 * | 2/2014 | Connor ............. A61B 17/7017 606/105 |
| 10,238,427 B2 * | 3/2019 | Wentz ................ A61B 17/7016 |

(Continued)

FOREIGN PATENT DOCUMENTS

| EP | 3366241 A1 * | 8/2018 | ......... A61B 17/7028 |
| FR | 2869524 A1 * | 11/2005 | ......... A61B 17/7025 |

*Primary Examiner* — Ellen C Hammond
(74) *Attorney, Agent, or Firm* — Hoffman Warnick LLC

(57) ABSTRACT

A vertebral assist device for monitoring, supporting, stabilizing, and adjusting vertebrae. An embodiment of the vertebral assist device includes: a plurality of vertebral support sections, each of the plurality of vertebral support sections configured to support a respective vertebra of a patient; an actuating system for interconnecting each adjacent pair of the plurality of vertebral support sections, the actuating system dynamically controlling an alignment of the plurality of vertebral support sections; and a control system for actively monitoring the alignment of the plurality of vertebral support sections and for directing the actuating system to dynamically adjust the alignment of the plurality of vertebral support sections until an alignment goal is achieved.

19 Claims, 8 Drawing Sheets

(52) U.S. Cl.
CPC ............ *A61B 2017/00221* (2013.01); *A61B 2017/00734* (2013.01); *A61F 2002/48* (2013.01)

(56) References Cited

U.S. PATENT DOCUMENTS

| | | | |
|---|---|---|---|
| 2007/0232958 A1* | 10/2007 | Donofrio | A61B 5/0031 600/587 |
| 2009/0125062 A1* | 5/2009 | Amin | A61B 17/7017 606/246 |
| 2014/0303539 A1* | 10/2014 | Baym | A61B 8/0875 602/23 |
| 2016/0262800 A1* | 9/2016 | Scholl | A61B 17/7011 |
| 2016/0270825 A1* | 9/2016 | Wentz | A61B 17/7016 |
| 2020/0197048 A1* | 6/2020 | Suddaby | A61B 17/7011 |

* cited by examiner

VERTEBRAL ASSIST SPINAL MEDICAL DEVICE

TECHNICAL FIELD

The disclosure generally relates to a medical device and related treatment. More particularly, the disclosure relates to a medical vertebral assisting device for treating, supporting, and stabilizing vertebrae.

BACKGROUND

Approximately half of the population of the United States population suffers from chronic back complications causing discomfort and pain, while about 300,000 people live with vertebro-spinal injuries resulting in paralysis and other permanent disabilities or limitations. In addition, around 5 million people suffer from varying degrees of scoliosis.

The spinal column is comprised of twenty-four independently moving vertebrae that allow for proper motion and flexibility. The vertebrae, along with a membrane called the meninges, provide natural protection of the delicate nervous system that serves to maintain bodily functions and movement. When part of the spine is impeded or damaged due to injury or disease, it may not be able to properly relay signals to the target extremities. This may result in loss of movement, bowel or bladder control issues, vital organ dysfunction, involuntary spasms, pain or burning in the areas affected, difficulty breathing, and severe chronic pain. Common causes of such problems include not only vertebral or spinal cord injuries caused by serious falls or automobile accidents, but scoliosis as well.

Scoliosis is a form of spinal misalignment that can cause nerve compression and surrounding muscular fibers to atrophy over time. If left uncorrected, serious long-term damage can lead to spinal deterioration, musculo-skeletal remodeling, chronic pain, nerve interference, and disc degeneration resulting in limited range of motion, coordination issues, incontinence, and a decreased quality of life.

Many people are unaware that they have a scoliosis until symptoms set in due to pronounced degrees of exaggerated kyphosis or lordosis (curvatures of the spinal column). Early development can be asymptomatic. It can take years for the symptoms to manifest. Diagnosing the problem early is critical to preventing serious or permanent damage that could impede the body's maintenance and innate healing abilities.

There are many types of procedures to correct such spinal issues, including spinal fusions, vertebral disc replacements or discectomies, and conventionally used vertebral rod stabilizers (pedicle screw systems). In addition, many pedicle screw systems are simply implanted to stabilize vertebrae while they fuse. After fusion, the pedicle screw system is typically left in the patient with no further functionality. Unfortunately, long-term side-effects may persist that include a limited range of motion due to fixation or fusion, scar tissue build-up as a result of repeated interventions or excessive damage during procedure, or other complications such as symptom recurrence or newly developed problems above or below the surgery site.

Even with these methods, some patients may not respond well or prefer alternative solutions, which may not adequately address their particular spinal issues. Additionally, these procedures may not offer long-term corrections. For example, across various methods of performing discectomies, there is about a 30% recurrence rate, resulting in repeated surgical reintervention. In many cases, reintervention may result in increased or pronounced instability in the affected areas. As a consequence of reintervention or failed primary intervention, the risk of disc slippage, degeneration, vertebral instability, and lumbar herniation may increase.

Currently, across most conventionally used spinal corrective procedures, there is about a 55% recurrence rate of complication 5-7 years after initial intervention. For laminectomies however, the recurrence rates are about 25% after 5-7 years. Unfortunately, as the population increases, so too does the number and percentage of recurrence rates for these procedures.

SUMMARY

A first aspect of the disclosure is directed to a vertebral assist device, including: a plurality of vertebral support sections, each of the plurality of vertebral support sections configured to support a respective vertebra of a patient; an actuating system for interconnecting each adjacent pair of the plurality of vertebral support sections, the actuating system dynamically controlling an alignment of the plurality of vertebral support sections; and a control system for actively monitoring the alignment of the plurality of vertebral support sections and for directing the actuating system to dynamically adjust the alignment of the plurality of vertebral support sections until an alignment goal is achieved.

A second aspect of the disclosure is directed to a method for stabilizing and aligning vertebrae, including: attaching a plurality of vertebral support sections to a set of vertebra of a patient, each of the plurality of vertebral support sections configured to support a respective vertebra of the patient; interconnecting each adjacent pair of the plurality of vertebral support sections using the actuating system, the actuating system dynamically controlling an alignment of the plurality of vertebral support sections; and implanting a control system into the patient, the control system actively monitoring the alignment of the plurality of vertebral support sections and directing the actuating system to dynamically adjust the alignment of the plurality of vertebral support sections until an alignment goal is achieved.

The details of one or more embodiments are set forth in the accompanying drawings and the description below. Other features, objects and advantages will be apparent from the description and drawings, and from the claims.

BRIEF DESCRIPTION OF THE DRAWINGS

These and other features of this invention will be more readily understood from the following detailed description of the various aspects of the invention taken in conjunction with the accompanying drawings.

Figure 1D:
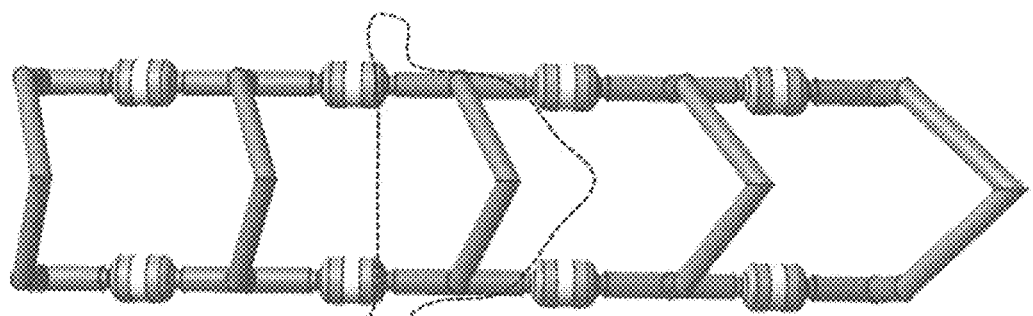
FIGS. 1A-1D depict various views of a medical vertebral assisting device attached to the vertebrae of a patient according to embodiments, with FIG. 1A depicting an anterior view of the attached device, FIG. 1B depicting a lateral-anterior view of the attached device, FIG. 1C depicting a lateral-posterior view of the attached device, and FIG. 1D depicting a posterior view of the attached device.

The drawings are not necessarily to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements.

DETAILED DESCRIPTION

The disclosure generally relates to a medical device and related treatment. More particularly, the disclosure relates to a medical vertebral assisting device for treating, supporting, and stabilizing vertebrae.

The medical vertebral assisting device disclosed herein provides a long-term solution for restoring wellness to those suffering from traumatic vertebro-spinal injuries, scoliosis, and other spinal issues. Some of the benefits provided by the medical vertebral assisting device include, for example:

1) Enables surgeons and medical professionals to treat patients that may have not been suitable candidates for other devices/procedures;
2) Provides a smaller, custom built and fitted device that offers active corrections (self-adjustments) to preserve spinal integrity and mitigate problem recurrences, including new problems above or below the surgical/injury site;
3) Offers a longer term solution compared to previously available devices/procedures;
4) The artificial intelligence (AI) components of the device, in conjunction with the sensor and actuator systems, provide the patient with more mobility, an optimal range of motion, and as least the same weight bearing load as previously available devices.
5) The device software utilizes machine learning programming to assess and provide accurate, real-time stabilization and support to the patient;
6) The attachment of the device to the vertebral body offers reduced stress to the interface, thus decreasing the risk of hardware failure caused by mechanical stresses;
7) Unlike conventionally used vertebral pedicle screw systems, the device continuously and actively monitors and provides corrective support and stabilization to adversely affected vertebrae;
8) Provides a cost-effective solution for patients suffering from vertebral damage or scoliosis by providing real-time, automatic and continuous corrective measures to the spinal column during movement and while at rest;
9) Provides proper vertebral alignment, stabilization, and support during the patient's regular activities, improving the patient's quality of life.

According to an embodiment, the medical vertebral assisting device is an electro-servo-mechanical vertebral-assist device that attaches to a section of a patient's damaged/affected vertebrae. It is a self-adjusting, position-aware, self-learning smart-assist device that monitors and senses vertebral positions during patient movement in accordance with a baseline spinal alignment profile of the patient and in conjunction with accepted medical standards. Active vertebral stabilization is provided via a series of sensors and rotor assemblies that communicate with a master chip. The actuators may include low-frequency radio-frequency (RF) and/or ultrasonic (US) sensors, and may include a built-in microchip (e.g., similar to an "active" RFID tag). The actuators are configured to respond to excitation signals by performing a positional adjustment/stabilization procedure. The actuators include a transducer mechanism that senses an excitation signal and converts electrical energy into mechanical energy to drive the adjustment. A status signal is sent back to the master chip after positional adjustment is performed (incrementally, as needed) until the constraints on adjustment are reached.

The insertion of the medical vertebral assisting device may be accomplished, for example, using the accepted standards practiced by surgeons today to implant pedicle screws. The device may be inserted as fitted sections/components into the patients back and pedicle screwed into to the spinal column at the affected vertebrae. The sections of the medical vertebral assisting device are attached to both hemispheres of the affected vertebral bodies and both hemispheres of the spinous process (SP), meeting at the tip of the SP.

The medical vertebral assisting device is not intended to replace the vertebra(e) in whole or in part. Rather, the device is designed to assist existing vertebra(e) by actively monitoring, maintaining, stabilizing, and supporting the vertebra (e) during activity and movement based on a patient's unique skeletal structure through machine learning.

Figure 1C:
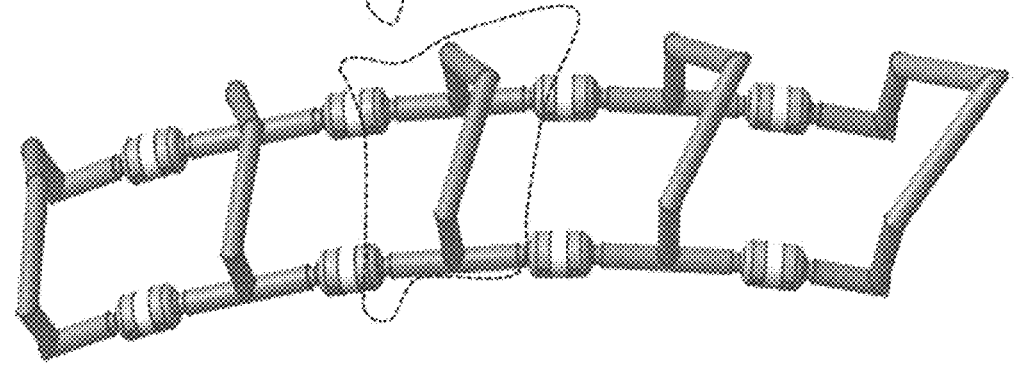
Figure 1B:
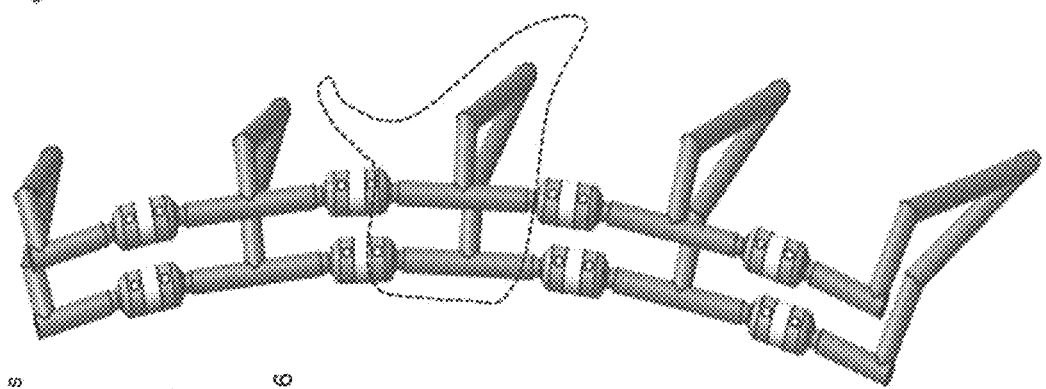
Figure 1A:
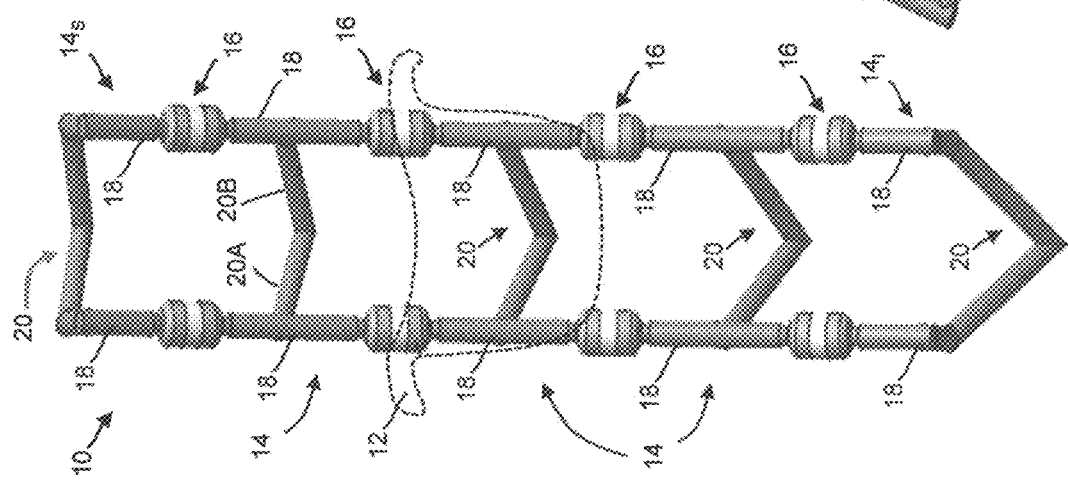

Referring now to the drawings, FIGS. 1A-1D depict various views of a medical vertebral assisting device 10 attached to the vertebrae 12 (only one is shown in each of FIGS. 1A-1D for clarity) of a patient according to embodiments. FIG. 1A depicts an anterior view of the attached device 10, FIG. 1B depicts a lateral-anterior view of the attached device 10, FIG. 1C depicts a lateral-posterior view of the attached device 10, and FIG. 1D depicts a posterior view of the attached device 10.

The medical vertebral assisting device 10 is formed using a plurality of individual vertebral support sections 14 (five (5) total in FIGS. 1A-1D). Each vertebral support section 14 is attached to a respective vertebra 12 of the patient. The number of vertebral support sections 14 employed in an application of the device 10 will generally depend on the specific medical needs and treatment plan for a given patient, and may vary from one use case to another. Each vertebral support section 14 of the medical vertebral assisting device 10 is designed (e.g., sized) to conform to a respective vertebra 12 of the patient.

Each vertebral support section 14 is connected to an adjacent vertebral support section 14 of the device 10 by a plurality of actuators 16 (e.g., electro-servo-mechanically controlled actuators). Vertebral support section 14s refers to the superior (highest) portion on the device 10 (i.e., the superior portion of the device 10 is located at the top with respect to its location along a patient's vertebrae). Vertebral support section 14i refers to the inferior (lowest) portion on the device 10 (i.e., the inferior portion is located at the bottom of the device 10 with respect to its location along a patient's vertebrae).

The vertebral support section 14 includes a plurality (a pair in this example) of connecting rods 18 and an extension member 20. As shown at least in FIGS. 1A and 2, the connecting rods 18 are secured to opposite lateral sides of a vertebra 12. The extension member 20, which is also secured to the vertebra 12, extends between the connecting rods 18 on the opposite lateral sides of the vertebra 12 to (and possible wrapping around) the spinous process (fin-like) area 22 (FIG. 2) of the vertebra 12. Together, when secured to the vertebra 12, the connecting rods 16 and extension member 20 act as a support framework for the vertebra 12.

In some embodiments, the vertebral support section 14 may be provided/assembled as a single component prior to being inserted and attached to the vertebra 12 of the patient. In other embodiments, the extension member 20 of the vertebral support section 14 may be formed as a single component prior to being inserted and attached to the connecting rods 18 and the vertebra 12 of the patient. Further, the extension member 20 itself may be formed using a combination and/or interconnection of individual extension rod segments (e.g., 20A, 20B). The connecting rods 18 and extension member 20 may be secured together using, for example, screws or the like. The sizes and configurations of the vertebral support sections 14 in the medical vertebral assisting device 10 will generally vary along a patient's spinal column to accommodate different sized vertebrae 12, to provide varying degrees of vertebral support, and/or to address different spinal issues.

The connecting rods 18 and extension member 20 of each vertebral support section 14 of the medical vertebral assisting device 10 may be inserted into a patient (e.g., laparoscopically via the neck or back), interconnected/fitted as necessary, and secured to the vertebra 12 (e.g., using pedicle screws, an adhesive, and/or using any other medically approved attachment methodology). In some cases, the vertebral support sections 14 may be preassembled and fitted to a patient's vertebrae prior to being inserted into the patient. It should be noted that the spinal column of the patient is not entered during the implantation of the device 10 into a patient.

As will be presented in greater detail below, opposing distal ends of respective connecting rods 18 of adjacent vertebral support sections 14 of the device 10 are coupled to the actuators 16, which are positioned adjacent vertebral discs 24 (FIG. 2) of the patient. In operation, the actuators 16 allow for omnidirectional rotation for proper vertebral stabilization in response to a patient's (vertebral) movement, assist in actively stabilizing the patients vertebrae, and provide an optimal range of axial and torsional motion. The actuators 16 may be attached to the distal ends of the connecting rods 18 prior to, during, and/or after the insertion and/or attachment of the connecting rods 18 to the vertebra 12 of the patient.

In some embodiments, the connecting rods 18 and/or extension member 20 of a vertebral support section 14 may be formed of an alloy of cobalt-59, which provides resistance to heat, corrosion, moisture, and wear over time. The components may be adhered to the vertebrae 12 using a substance similar to that used to adhere braces to teeth. In other embodiments, the connecting rods 18 and/or extension member 20 of a vertebral support section 14 may be screwed into the vertebrae 12 (e.g., similar to a pedicle screw method). Both of these techniques mitigate risks in surgery such as bone fragments or spinal cord damage.

Figure 2:
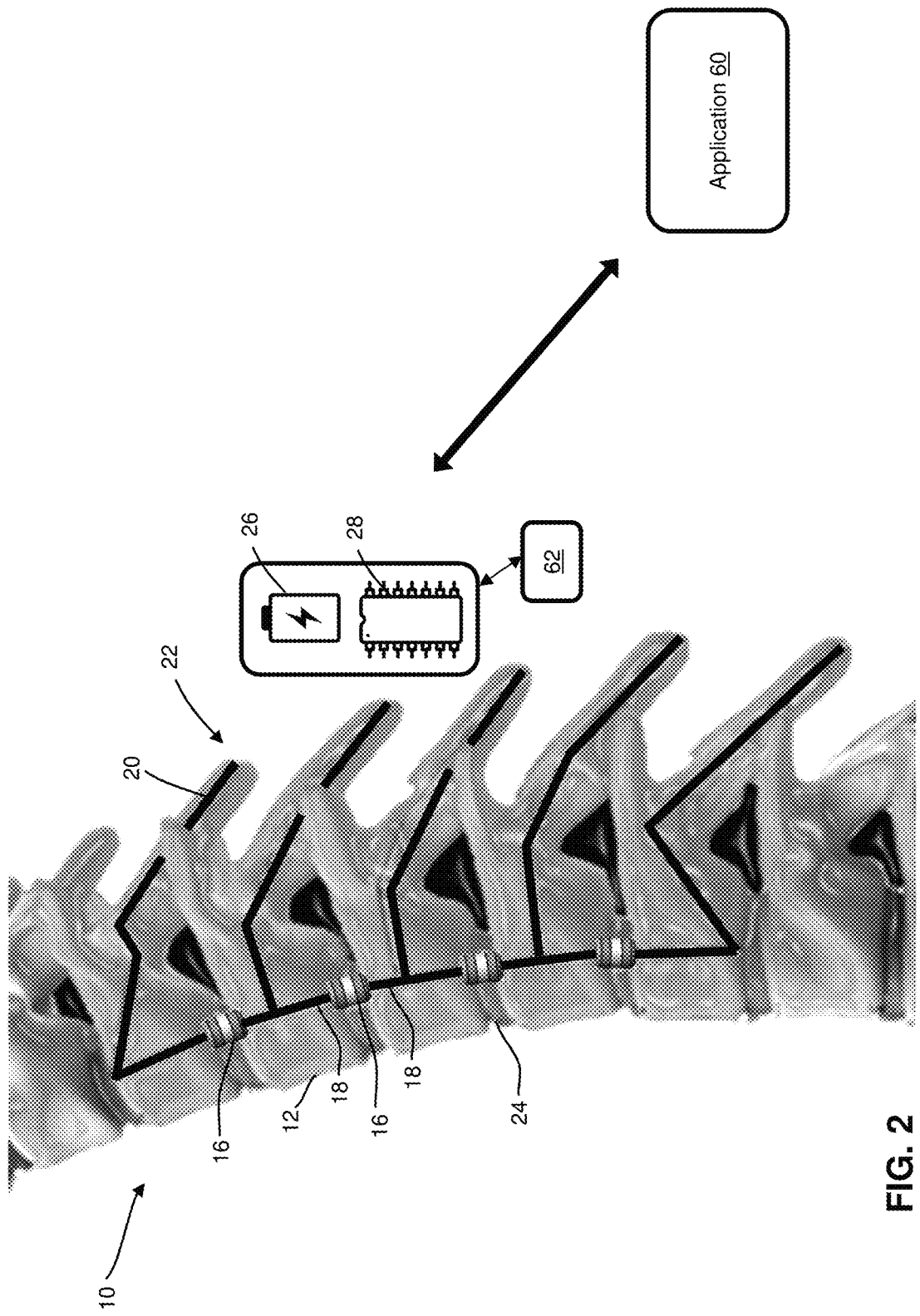
FIG. 2 depicts a medical vertebral assisting device attached to the vertebrae of a patient according to embodiments.
Figure 4:
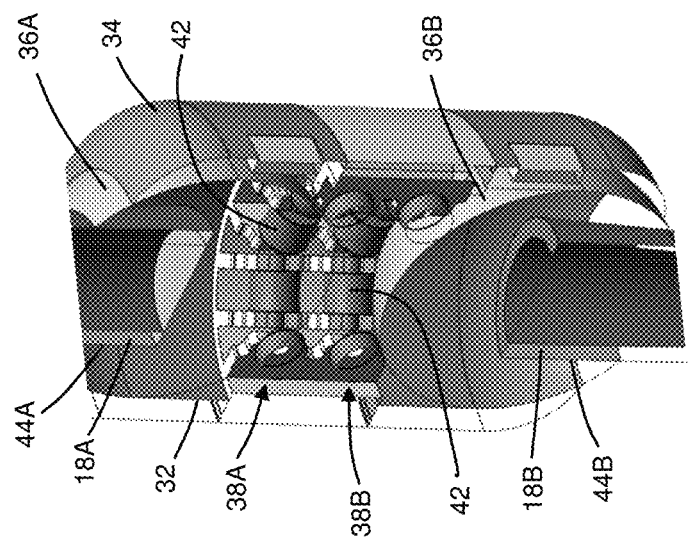
FIG. 4 depicts a partial cut-away view of the actuator of FIG. 3 according to embodiments.
Figure 3:
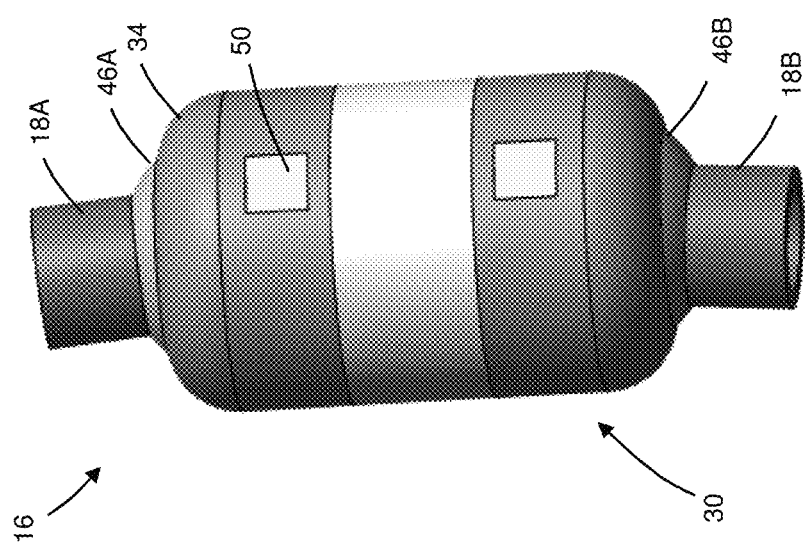
FIG. 3 depicts an actuator of a medical vertebral assisting device according to embodiments.
Figure 6:
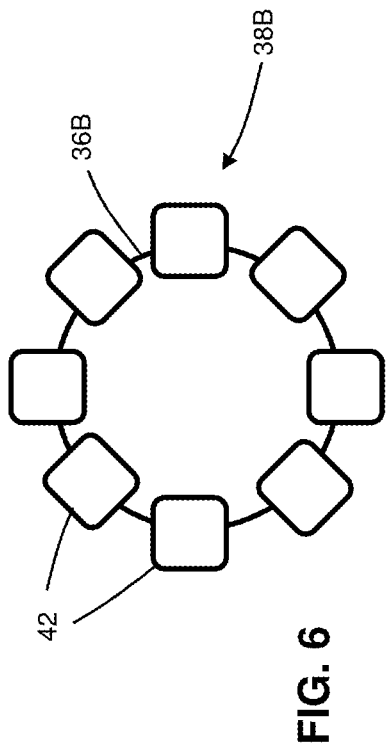
FIG. 6 is a cross-sectional view of the actuator of FIG. 4 taken along line 6-6 in FIG. 5 according to embodiments.

The components of the medical vertebral assisting device 10 may be powered by a battery 26 (FIG. 2). For example, a long-lasting lithium-ion battery, which can be easily replaced via a small incision through the patient's skin (akin to how batteries are used in heart pacemaker implants, but less invasive and considerably smaller), may be used. The battery 26 and a master chip 28 for controlling the operation of the components of the medical vertebral assisting device 10 may be inserted/positioned subcutaneously in the patient and encased in a polyethylene packet for safety. This will encourage a rapid recovery and will not encumber the patient from performing regular activities.

An actuator 16 according to embodiments is depicted in greater detail in FIGS. 3-7. The actuator 16 includes a dual-layer housing 30 having an inner housing 32 enclosed within an outer housing 34.

Figure 5:
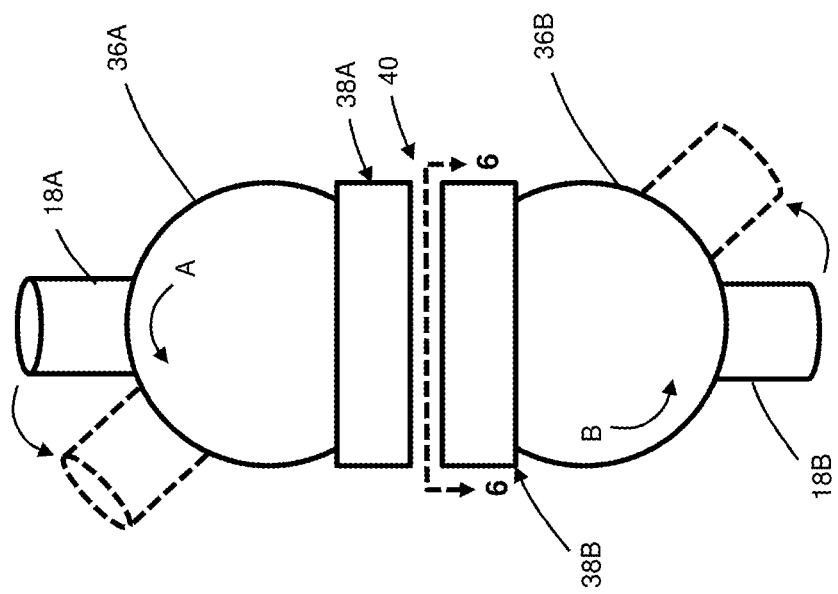
FIG. 5 depicts another view of the actuator of FIG. 4 according to embodiments.

Each actuator 16 includes balls 36A and 36B, which are housed within the inner housing 32 and separated by a small interspaced void 40 (FIG. 5). The balls 36A, 36B are independently and omnidirectionally rotatable by respective rotor assemblies 38A, 38B. Opposing distal ends of respective connecting rods 18 of adjacent vertebral support sections 14 of the device 10 are coupled to the balls 36A, 36B of the actuator 16. The inner housing 32 is configured to provide a socket-type enclosure to house each of the balls 36A, 36B and to allow rotation of the balls 36A, 36B, therein.

As shown, a distal end of a connecting rod 18A of a first vertebral support section 14 of the device is positioned within an opening 44A formed in the ball 36A, while a distal end of a connecting rod 18B of a second, adjacent vertebral support section 14 of the device 10 is positioned within an opening 44B formed in the ball 36B. The connecting rods 18A, 18B extend out of openings 46A, 46B provided in opposite ends of the outer housing 32. In this configuration, a rotation of the ball 36A by the rotor assembly 38A in a particular direction results in a corresponding displacement of the connecting rod 18A in the direction of rotation. Similarly, a rotation of the ball 36B by the rotor assembly 38B in a particular direction results in a corresponding displacement of the connecting rod 18B in the direction of rotation. Such rotation/displacement is shown in phantom in FIG. 5, where ball 36A has been rotated in direction "A" by the rotor assembly 38A and ball 36B has been rotated in direction "B" by the rotor assembly 38B. As detailed above, the balls 36A, 36B can be rotated independently of one other by their respective rotor assemblies 38A, 36B.

The rotor assembly 38A includes a plurality of individually controllable rotors 42 that are disposed about, and in contact with, a surface of the ball 36. Likewise, the rotor assembly 38B includes a plurality of individually controllable rotors 42 that are disposed about, and in contact with, a surface of the ball 36B. In the embodiment depicted in FIGS. 3-6, each rotor assembly 38A, 38B includes eight (8) individual rotors 42 arranged in a ring about the balls 36A, 36B. The number and/or type of rotors 42 may vary from embodiment to embodiment, depending on, for example, the force requirements for the actuator 16 and the degree of rotational control of the balls 36A, 36B.

In some embodiments, multi-degree-of-freedom, omnidirectional piezoelectric rotors 42 may be used to provide controlled, complex, precise, and fast motions. A structurally controlled omnidirectional soft cylindrical rotor may be fabricated in a modular way using multilayer composite of polylactic acid based conductive graphene, shape memory polymer, shape memory alloy, and polyurethane.

According to some embodiments, the distal ends of the connecting rods 18A, 18B may be fixedly secured within the openings 44A, 44B in the balls 36A, 36B. In other embodiments, however, the distal ends of the connecting rods 18A, 18B may be configured to move (e.g., extend and retract) a short distance (e.g., by up to one-inch (within 10% tolerance)) into and out of the openings 44A, 44B in the balls 36A, 36B in a passive telescoping manner (e.g., during movement of the patient). The passive telescoping of the connecting rods 18A, 18B increases the range of motion of the patient in response to, for example, flexion, internal (body) pressures, and vertebral position(s) of the patient during movement. A portion of the distal end of each connecting rod 18A, 18B remains within the openings 44A, 44B in the balls 36A, 36B.

Figure 7:
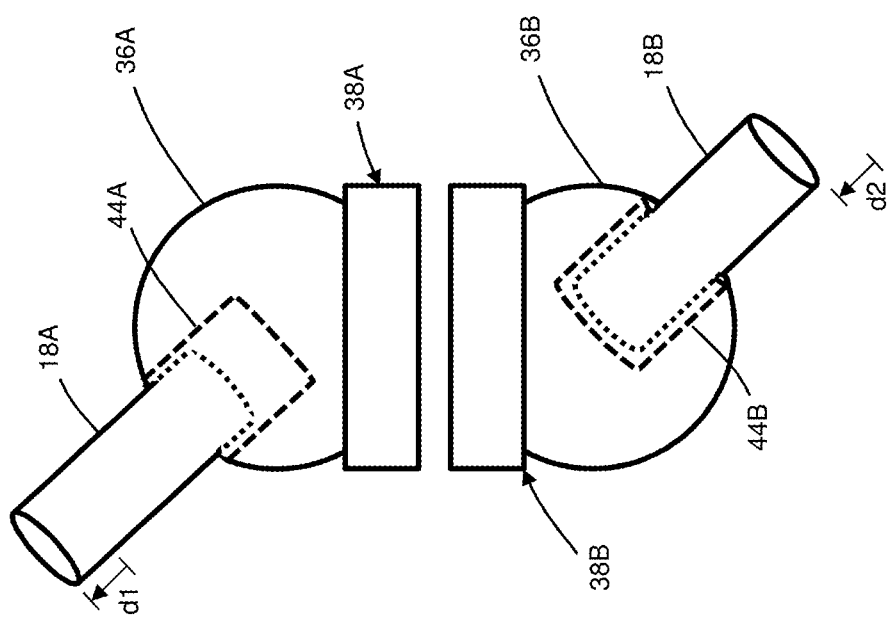
FIG. 7 depicts another view of the actuator of FIG. 4 according to embodiments.

An example of the passive telescoping of the connecting rods 18A, 18B is depicted in FIG. 7. In this example, the balls have been rotated as described with reference to FIG. 5. In addition to the rotation of the balls 18A, 18B and resultant displacement of the connecting rods 18A, 18B shown in FIG. 5, the distal end section of the connecting rod 18A has extended (passively) a short distance d1 out of the opening 44A in the ball 18A, while the connecting rod 18B has retracted (passively) a short distance d2 into the opening 44B in the ball 18B. As such, the exposed portion of the connecting rod 18A is longer than the exposed portion of the connecting rod 18B. In addition, a portion of the distal end of each connecting rod 18A, 18B remains within the openings 44A, 44B in the balls 36A, 36B.

Referring again to FIG. 3, each actuator 16 includes a sensor/transducer 50 that may be embedded in the outer housing 34. The sensor/transducer 50 of each actuator 16 is coupled to the rotor assemblies 38A, 38B and the master chip 28 via wireless and/or wired connections.

The sensor/transducer 50 may include low-frequency radio-frequency (RF) and/or ultrasonic (US) sensors, and may include a built-in microchip (e.g., similar to an "active" RFID tag). Each actuator 16 is configured to respond to an excitation signal output by master chip 28 and sensed by the sensor/transducer 50 by performing a positional adjustment/stabilization procedure via operation of the rotor assemblies 38A, 38B. The sensor/transducer 50 senses the excitation signal and converts electrical energy into mechanical energy to drive the rotor assemblies 38A, 38B to attain the requested adjustment. A status signal is sent by the sensor/transducer 50 back to the master chip 28 after positional adjustment is performed (incrementally, as needed) until the constraints on adjustment are reached.

As stated above, in some embodiments, the connecting rods 18 and/or extension member of a vertebral support section 14 may be formed of an alloy of cobalt-59, which provides resistance to heat, corrosion, moisture, and wear over time. The gears that power the rotor assemblies 38A, 38B of each actuator 16 may also be formed of an alloy of cobalt-59

A polyethylene, titanium-alloy material, or cobalt-chromium material may be used to produce the ball-and-socket components of the actuator 16. The use of metals other than titanium will ensure that the connecting rods 18 and extension members 20 do not fuse with the patient's vertebrae post procedure. This will allow for easier replacement of parts if the need arises. In other embodiments, a titanium alloy may be used to form the connecting rods 18, extension members 20, and/or the gears that power the rotor assemblies 38A, 38B of each actuator 16.

An application 60 (FIG. 2) can be connected (e.g., via a wireless or wired connection) to the master chip 28 to obtain diagnostic information and to program, control, monitor, and calibrate the medical vertebral assisting device 10. For example, a medical professional may wirelessly communicate with the master chip 28 of the medical vertebral assisting device 10 via the application 60 running on a smart phone, tablet, or computer, eliminating the need to surgically correct or change the position of the medical vertebral assisting device 10 to maintain vertebral stabilization and support. The master chip 28 may include or be coupled to a transducer 62 that is configured to sense a signal (e.g., ping) sent from the application 60 and to provide diagnostic information to the application 60 or perform other functions in response to the signal.

The medical vertebral assisting device 10 is configured to adapt to any new physical changes in a patient's vertebra(e). The application 60 can be used at any time to (e.g., wirelessly) recalibrate, update, or reinstall the AI programming used by the master chip 28 to control the actuators 16 of the medical vertebral assisting device 10. Through these capabilities, the medical vertebral assisting device 10 is capable of automatically maintaining, stabilizing, and correcting vertebral positions during movement for those who do not successfully respond to alternative methods of corrective care.

According to embodiments, a software-based machine learning solution may be used by the medical vertebral assisting device 10 to assess and provide accurate, real-time stabilization and support to a patient. A pre-trained, default software model designed to solve a particular type of spinal stabilization problem in a digitally modeled spine environment may initially be uploaded onto the master chip 28. The default model is independent of the patient that the medical vertebral assisting device 10 will be deployed in. After a patient has been identified/diagnosed, several modes of learning may be used to update (using any suitable learning process) the default model stored in the master chip 28. A first mode uses a digital model of the patient's spine (e.g., obtained via X-ray or fluoroscopy). In a second mode, a post-operation model is developed through continuous learning after the medical vertebral assisting device 10 is deployed in the patient. In a third mode, modes 1 and 2 are combined.

A medical professional may monitor the patient, update the model in the master chip 28, and control the degree to which the model is updated using the application 60—all without having to remove and reinsert the medical vertebral assisting device 10. Training of the model once the medical vertebral assisting device 10 has been deployed in the patient can be performed as part of a post-operation therapy procedure.

Figure 8:
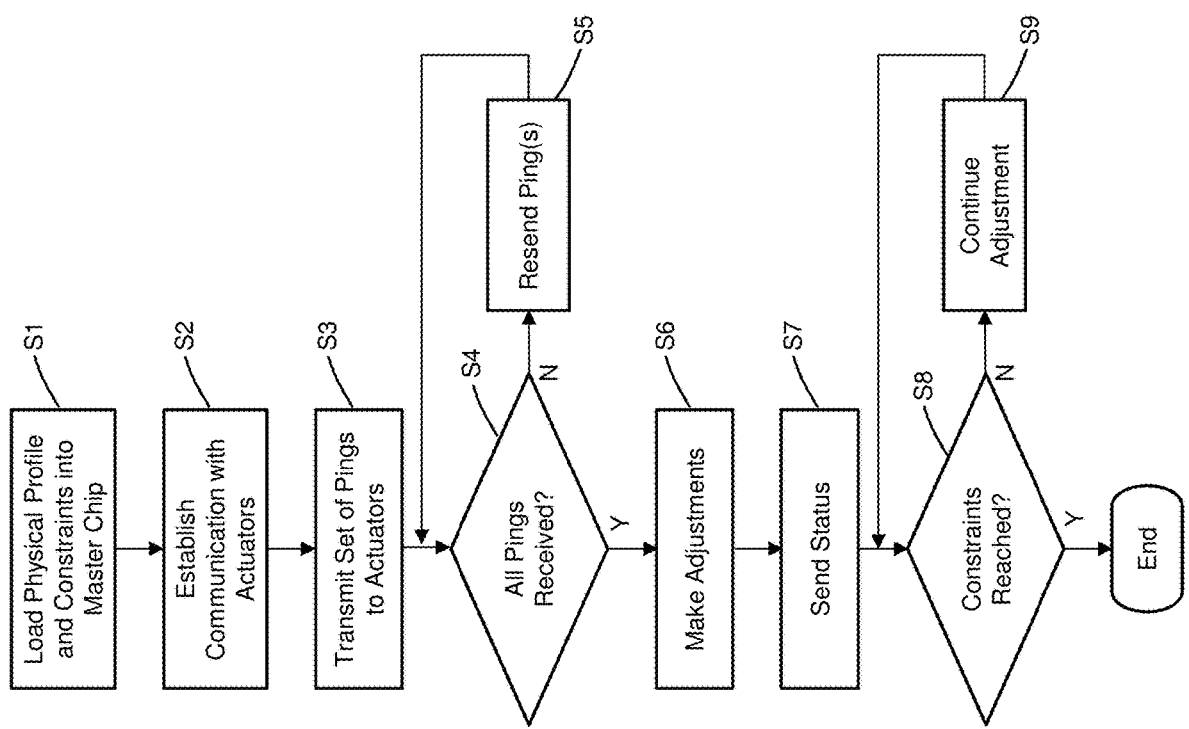
FIG. 8 depicts a process for the control of the medical vertebral assisting device according to embodiments.

A process for the control of the medical vertebral assisting device 10 according to embodiments is depicted in FIG. 8. A machine learning or machine-to-machine (M2M) approach is used where the master chip 28 monitors and adjudicates the (re)positioning of the actuators 16 within learned and preprogrammed constraints and learns about how to maintain the proper posture for a patient. The AI and machine learning algorithms may be written using a software program such as Python or C++.

At S1, the patient's physical profile and alignment constraints (e.g., provided by a medical professional) are loaded into the master chip 28. At S2, the master chip 28 establishes communication with the actuators 16 of the medical vertebral assisting device 10. At S3, the master chip 28 transmits a set of pings to the actuators 16. If any actuator 16 does not receive a ping (NO at S4), the actuator 16 sends a request at S5 to the master chip 28 to resend the ping. Once all of the actuators 16 have successfully received a ping (YES at S4), each actuator 16 makes any required adjustments at S6 and sends a status message to the master chip 28 at S7 after positional adjustment is performed (incrementally, as needed at S9), until the constraints on adjustment are reached (YES at S8).

As detailed above, each actuator 16 includes a built-in microchip and a sensor/transducer 50 configured to receive a low RF/US excitation signal in the form of a ping. Each actuator 16 is configured to respond to a given excitation signal by performing a predetermined positional adjustment/stabilization procedure via operation of the rotor assemblies 38A, 38B. The sensor/transducer 50 senses the excitation signal and converts electrical energy into mechanical energy to drive the rotor assemblies 38A, 38B to attain the requested adjustment. This wireless send/reply process requires very little power. Each actuator 16 is programmed to receive and respond to a plurality of different excitation signals, where each excitation signal corresponds to a specific set of adjustments to be carried out by the rotor assemblies.

Figure 9:
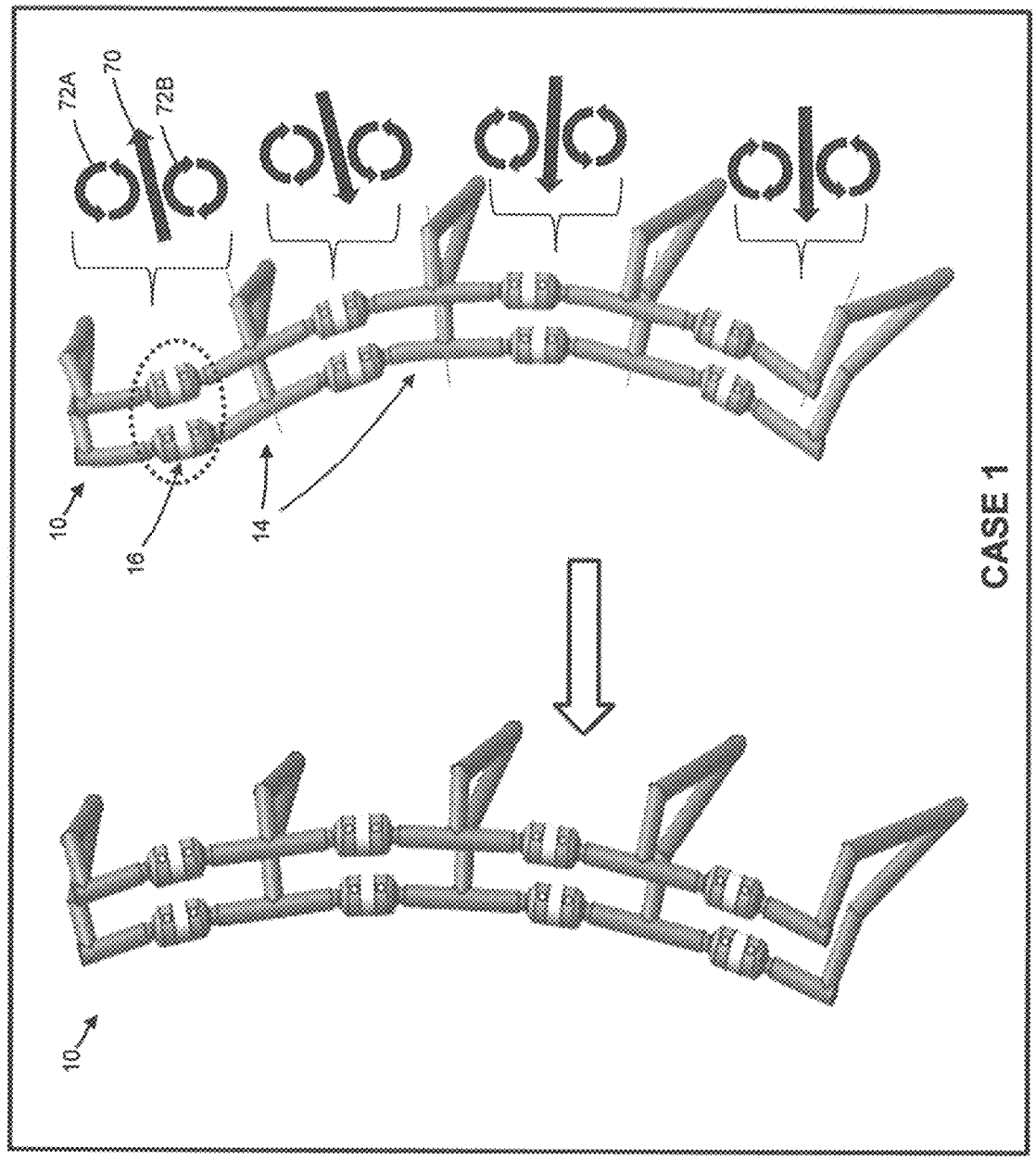
FIG. 9 depicts a first use case for the medical vertebral assisting device according to embodiments.

A first use case (Case 1) of the medical vertebral assisting device 10 is depicted on the right side of FIG. 9, and an alignment goal of the device 10 is depicted on the left side of FIG. 9. In Case 1, a patient suffers from exaggerated scoliosis. The device 10 uses preprogramming and self-learning algorithms to progressively realign the spine and maintain posture. In addition, the device 10 actively monitors and assess stability efforts to continuously perform omnidirectional corrective actions on a real-time basis. The arrows 70 on the right side of FIG. 9 indicate the force vector sum applied by each corresponding pair of actuators 16 to the adjacent vertebral support sections 14 (and thus to the vertebrae 12 supported by the adjacent vertebral support sections 14) to counteract and correct the patient's improper vertebral alignment. The arrows 72A, 72B indicate the corresponding direction of rotation of the balls 36A, 36B in the pair of actuators 16.

Figure 10:
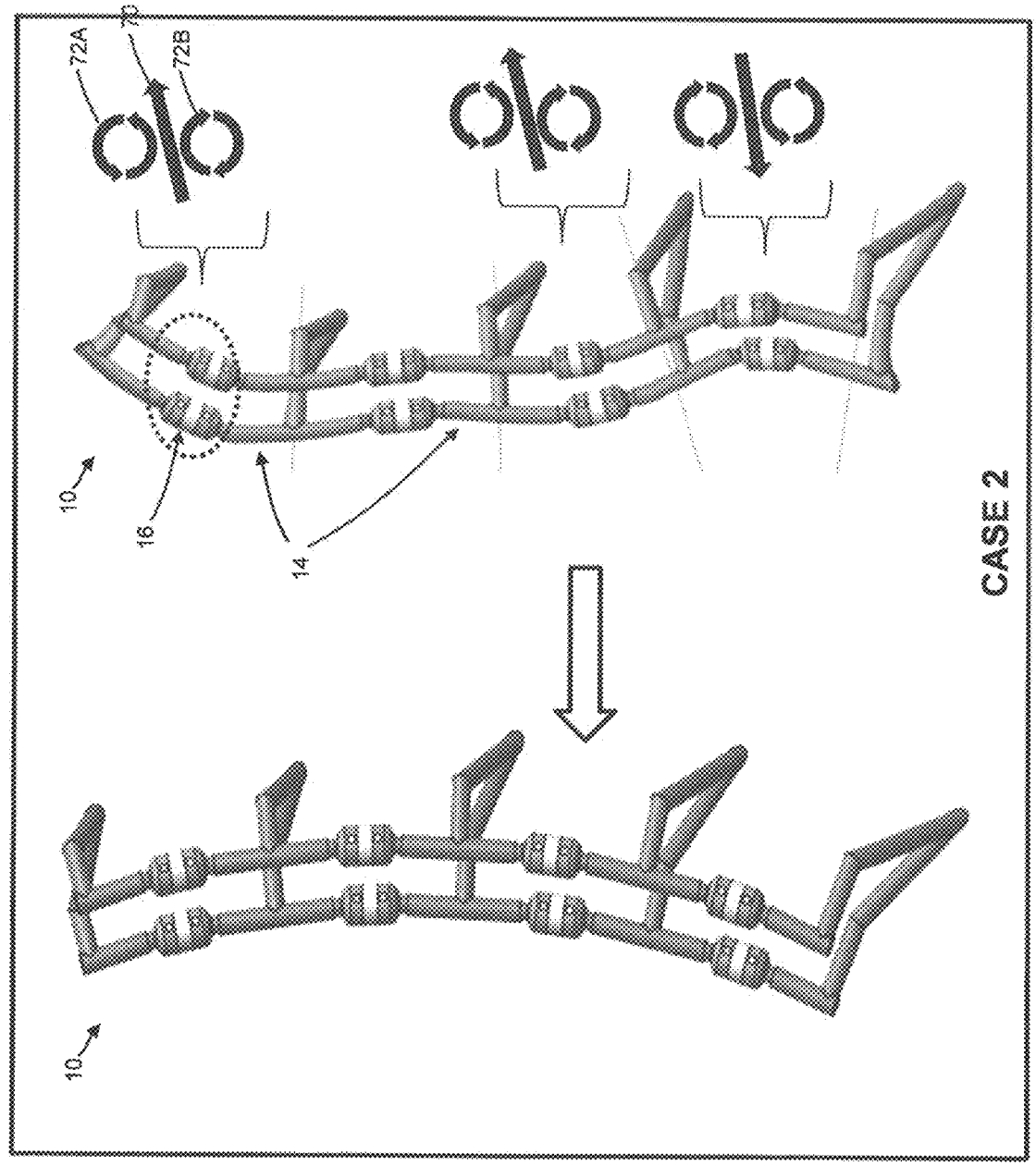
FIG. 10 depicts a second use case for the medical vertebral assisting device according to embodiments.

A second use case (Case 2) of the medical vertebral assisting device 10 is depicted on the right side of FIG. 10, and an alignment goal of the device 10 is depicted on the left side of FIG. 10. In Case 2, a patient suffers from severe spinal misalignment caused by trauma. Again, the device uses preprogramming and self-learning algorithms to progressively realign the spine and maintain posture. In addition, the device 10 actively monitors and assess stability efforts to continuously perform omnidirectional corrective actions on a real-time basis. As in FIG. 9, the arrows 70 on the right side of FIG. 10 indicate the force vector sum (if any) applied by each corresponding pair of actuators 16 to the adjacent vertebral support sections 14 (and thus to the vertebrae 12 supported by the adjacent vertebral support sections 14) to counteract and correct the patient's improper vertebral alignment, while the arrows 72A, 72B indicate the corresponding direction of rotation of the balls 36A, 36B in each pair of actuators 16.

In both Case 1 and Case 2, after the alignment goal of the device 10 has been achieved, the rotor assemblies 38A, 38B of the actuators 16 no longer operate to correct alignment, but instead to provide stability and support to the vertebrae. The rotor assemblies 38A, 38B will, however, rotate as necessary when the patient is performing regular activities to provide proper vertebral alignment, stabilization, and support, thus improving the patient's quality of life.

It should be noted that stabilization devices such as the medical vertebral assisting device 10 disclosed herein can be developed for other parts of the human body (i.e. knee, hip). Extending the proposed solution to other parts of the body requires the development of a digital model of that area of the body along with the appropriate objective function that would result in stabilization of that area of the body. Furthermore, the measurement capabilities of the device can also be used strictly as a monitoring system with analysis being done on board by an appropriate machine learning algorithm. The data can then be transmitted wirelessly back to an application used by the physician for viewing and analysis.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual skilled in the art are included within the scope of the invention as defined by the accompanying claims.

The invention claimed is:

1. A vertebral assist device, comprising:
   a plurality of vertebral support sections, each of the plurality of vertebral support sections configured to support a respective vertebra of a patient, wherein each vertebral support section includes a pair of connecting rods for attachment to opposite lateral sides of a vertebra and an extension member for attachment to the vertebra, the extension member connected to and extending between the connecting rods around the vertebra;
   an actuating system for interconnecting adjacent vertebral support sections, the actuating system dynamically controlling an alignment of the vertebral support sections; and
   a control system for actively monitoring the alignment of the plurality of vertebral support sections and for directing the actuating system to dynamically adjust the alignment of the plurality of vertebral support sections until an alignment goal is achieved.

2. The vertebral assist device according to claim 1, wherein the actuating system includes a plurality of pairs of actuators, each pair of actuators interconnecting adjacent vertebral support sections.

3. The vertebral assist device according to claim 2, wherein each actuator includes a communication component for wirelessly communicating with the control system, the communication component configured to receive alignment instructions from the control system and to transmit status information to the control system.

4. The vertebral assist device according to claim 3, wherein the alignment instructions include an excitation signal, and wherein the communication component of each actuator further includes a transducer for converting the excitation signal into mechanical energy for driving the actuator.

5. The vertebral assist device according to claim 4, wherein the excitation signal is a low frequency radio frequency (RF) or ultrasonic (US) signal.

6. The vertebral assist device according to claim 2, wherein each actuator further includes:
   a pair of independently and omnidirectionally rotatable balls, each ball coupled to a corresponding connecting rod of the adjacent vertebral support section; and
   a pair of rotor assemblies for independently rotating each ball and the connecting rod coupled thereto in response to alignment instructions received from the control system to affect a change in an alignment of the pair of adjacent vertebral support sections.

7. The vertebral assist device according to claim 6, wherein the end of each connecting rod is configured for passive movement partially into and out the ball coupled thereto.

8. The vertebral assist device according to claim 1, wherein the control system stores a physical profile and constraints on adjustment for the patient, and wherein the control system directs the actuating system to dynamically adjust the alignment of the plurality of vertebral support sections until the constrains on adjustment are reached.

9. The vertebral assist device according to claim 1, wherein the control system is configured to continuously monitor the actuating system and to dynamically adjust the alignment of the plurality of vertebral support sections in response to a change in alignment of the plurality of vertebral support sections.

10. The vertebral assist device according to claim 1, further comprising an external application for wirelessly communicating with the control system, wherein the external application is configured to program, control, monitor, and calibrate the control system.

11. A vertebral assist device, comprising:
a plurality of vertebral support sections, each of the plurality of vertebral support sections configured to support a respective vertebra of a patient;
an actuating system for interconnecting adjacent vertebral support sections, the actuating system dynamically controlling an alignment of the vertebral support sections;
a control system for actively monitoring the alignment of the plurality of vertebral support sections and for directing the actuating system to dynamically adjust the alignment of the plurality of vertebral support sections until an alignment goal is achieved; and
an external application for wirelessly communicating with the control system, wherein the external application is configured to program, control, monitor, and calibrate the control system.

12. The vertebral assist device according to claim 11, wherein the actuating system includes a plurality of pairs of actuators, each pair of actuators interconnecting adjacent vertebral support sections.

13. The vertebral assist device according to claim 12, wherein each actuator includes a communication component for wirelessly communicating with the control system, the communication component configured to receive alignment instructions from the control system and to transmit status information to the control system.

14. The vertebral assist device according to claim 13, wherein the alignment instructions include an excitation signal, and wherein the communication component of each actuator further includes a transducer for converting the excitation signal into mechanical energy for driving the actuator.

15. The vertebral assist device according to claim 14, wherein the excitation signal is a low frequency radio frequency (RF) or ultrasonic (US) signal.

16. The vertebral assist device according to claim 12, wherein each actuator further includes:
a pair of independently and omnidirectionally rotatable balls, each ball coupled to a corresponding connecting rod of the adjacent vertebral support section; and
a pair of rotor assemblies for independently rotating each ball and the connecting rod coupled thereto in response to alignment instructions received from the control system to affect a change in an alignment of the pair of adjacent vertebral support sections.

17. The vertebral assist device according to claim 16, wherein the end of each connecting rod is configured for passive movement partially into and out the ball coupled thereto.

18. The vertebral assist device according to claim 11, wherein the control system stores a physical profile and constraints on adjustment for the patient, and wherein the control system directs the actuating system to dynamically adjust the alignment of the plurality of vertebral support sections until the constrains on adjustment are reached.

19. The vertebral assist device according to claim 11, wherein the control system is configured to continuously monitor the actuating system and to dynamically adjust the alignment of the plurality of vertebral support sections in response to a change in alignment of the plurality of vertebral support sections.

\* \* \* \* \*